United States Patent
Yoon

(10) Patent No.: US 6,569,142 B1
(45) Date of Patent: May 27, 2003

(54) BIODEGRADABLE INFUSION SET

(75) Inventor: Yeo Saeng Yoon, Seoul (KR)

(73) Assignee: Boo Yoon Tech, Inc., Seoul (KR)

( * ) Notice: Subject to any disclaimer, the term of this patent is extended or adjusted under 35 U.S.C. 154(b) by 204 days.

(21) Appl. No.: 09/594,588

(22) Filed: Jun. 15, 2000

(30) Foreign Application Priority Data

Feb. 18, 2000 (KR) .......................................... 2000-7742

(51) Int. Cl.⁷ ............................................... A61B 19/00
(52) U.S. Cl. ...................................... 604/408; 604/403
(58) Field of Search ........................ 604/403, 408–410, 604/323, 326–28, 335; 528/272, 302, 308; 383/210.1; 220/62.22

(56) References Cited

U.S. PATENT DOCUMENTS

| | | | | |
|---|---|---|---|---|
| 4,439,598 A | * | 3/1984 | Sublett et al. ............ 528/295.3 |
| 5,391,644 A | * | 2/1995 | Yasuda et al. ......... 264/331.11 |
| 5,480,394 A | * | 1/1996 | Ishikawa ........................ 383/1 |
| 5,530,058 A | * | 6/1996 | Imaizumi et al. ............ 524/539 |
| 5,763,098 A | * | 6/1998 | Kameoka et al. ............ 428/481 |
| 5,834,582 A | * | 11/1998 | Sinclair et al. ............. 523/124 |
| 6,037,384 A | * | 3/2000 | Kakizawa et al. .......... 521/182 |
| 6,111,058 A | * | 8/2000 | Warzelhan et al. ......... 528/170 |

* cited by examiner

Primary Examiner—Angela D. Sykes
Assistant Examiner—Leslie R. Deak
(74) Attorney, Agent, or Firm—McGuireWoods LLP

(57) ABSTRACT

The present invention relates to a plastic infusion set. Unlike the conventional ones, the infusion set of the present invention is manufactured by using a novel biodegradable polyester resin composition with superior physical properties which thus can be degraded in nature without causing an environmental contamination and can also be applied in broader fields of medical industry.

7 Claims, 3 Drawing Sheets

BIODEGRADABLE INFUSION SET

BACKGROUND OF THE INVENTION

1. Field of the Invention

The present invention relates to a biodegradable infusion set and more particularly, to a biodegradable infusion set manufactured by using a novel polyester resin composition under specific injection and extrusion molding conditions, which thus can be disposed of without causing environmental contamination.

2. Description of the Related Art

In general, biodegradable resins have been welcomed worldwide since they can be disposed of without causing environmental contamination and thus their uses are on the gradual increase these days.

There have been known various kinds of biodegradable resins so far; however, their applications to commercial products have been much limited because their physical properties, molecular weight and biodegradability are not suitable for good molding and quality products.

The aliphatic polyester, known to have a good biodegradable property (J of Macromol. SCI-Chem., A-23(3), 1986, pp. 393–409), have been used as materials in medical, agricultural, fishing and packaging industries and its fields of applications are on gradual growth. However, the conventional type of aliphatic polyesters had disadvantages that their backbone structures were too soft and heat-labile, it had low crystallinity, low melting point, difficulty in molding due to high melt index, poor tensile strength and tear strength. To make these aliphatic polyesters more applicable, many efforts have been exerted to increase the number average molecular weight of the current aliphatic polyester to have more than 30,000, however, it has not been able to obtain aliphatic polyester having a molecular weight greater than 15,000 in the conventional polycondensation system.

As a way to solve these problems of conventional polyesters, a method of manufacturing aliphatic polyester resin having a number average molecular weight of greater than 30,000 by adjusting factors such as reaction temperature, degree of vacuum and amount of catalysts was disclosed in Korean Unexamined Patent Publication No 95-758; however, said aliphatic polyester resin had a low weight average molecular weight and was also heat-labile thus not considered appropriate in molding or forming.

In Korean Unexamined Patent Publication No 95-114171, a method of manufacturing aliphatic polyester with a high molecular weight by incorporating a monomer such as a polyhydric (at least tri-) alcohol or a poly (at least tri-) hydric carboxylic acid is disclosed. The above process provided a way to improve the molding and forming properties of the aliphatic polyester resin by introducing the monomers into the reactor to reduce the reaction time and to diffuse the molecules within the product. However, the application of this type of polyester resin was not easy due to the decrease of physical properties such as tensile strength resulted from the drastic increase in low molecular weight polyesters. Besides, the fact that the polyester resin easily becomes a gel type makes it difficult to control the reaction for preparing the polyester resin. There is still another process for increasing the molecular weight of the aliphatic polyester resin. Unexamined Korean Patent Publication No. 95-25072, which discloses the high molecular weight aliphatic polyester resin produced by an isocyanate as a coupling material reacting to an aliphatic polyester resin having a number average molecular weight of 15,000 to 20,000 which is produced by dehydration or de-glycol reaction of the mixture of main materials of (1) an aliphatic(including cyclic type), and (2) an aliphatic (including cyclic type) dicarboxylic acid(or an anhydride thereof with or without (3) a little of monomer of polyhydric alcohol or polyhydric carboxylic acid (or acid anhydride thereof). The aliphatic polyester resin obtained in this way had a number average molecular weight of 20,000 to 70,000. However, the above-mentioned process has a few drawbacks that it requires more reaction time thus resulting in poor productivity, and the isocyanate, a coupling material to increase the molecular weight of polyester resin, is known to be a carcinogen so necessitating an extremely careful handling of the ingredient.

The conventional infusion set consists of an infusion bag, a hose and the accessories made of plastic, and the disposal of said infusion sets after use has been quite costly. However, there has not been found a good resolution how to deal with the waste disposal of infusion sets nor the infusion sets ever manufactured by using biodegradable polyester resins.

SUMMARY OF THE INVENTION

The conventional infusion sets used in medical fields have been a cause of environmental contamination while its biodegradable versions have been experiencing the limited applications due to their poor physical properties. The object of the present invention is therefore to provide an infusion set which can not only be degraded in nature without causing an environmental contamination but can be also applied in broader fields of medical industry due to its superior physical properties.

DESCRIPTION OF THE PRESENT INVENTION

Figure 1:
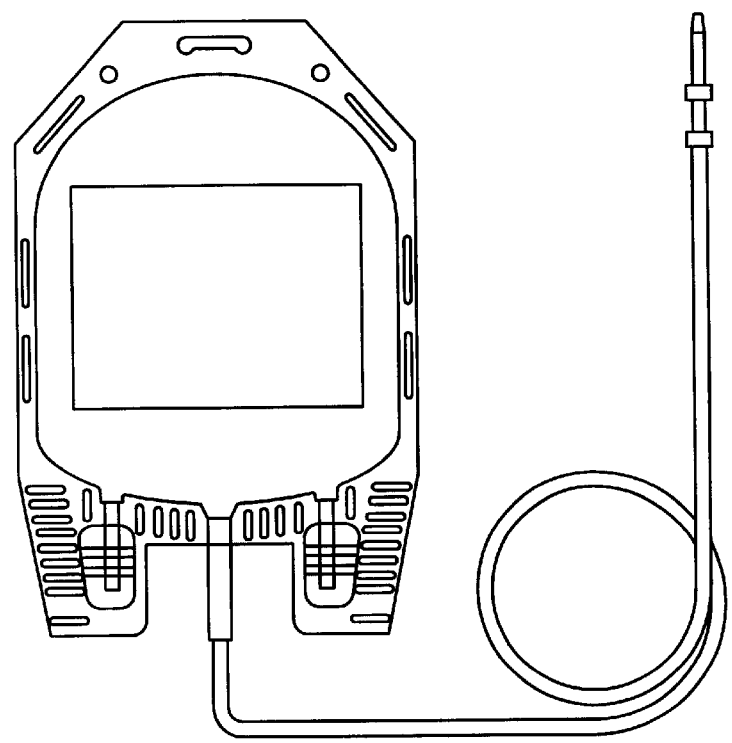
FIG. 1 shows the schematic view of one example of the biodegradable infusion sets manufactured according to the method of the present invention.

The present invention relates to a biodegradable plastic infusion set manufactured by means of injection molding and extrusion molding using polyester resin having 9,000–90,000 of number average molecular weight, 30,000–600,000 of weight average molecular weight, 40–150° C. of melting point, 0.1.–50 g/10 min of melt index (190° C., 2160 g).

The resin composition used in the present invention comprises an aromatic dicarboxlic acid(or an acid anhydride thereof) such as dimethyl terephthalate and terephthalic acid; an aliphatic (including cyclic type) dicarboxylic acid (or an acid anhydride thereof), one or more selected from succinic acid and adipic acid; and an aliphatic (including cyclic type) glycol, one or more selected from 1,4-butanediol and ethylene glycol, by means of esterification and polycondensation reactions as disclosed in Unexamined Korean Patent Publication Nos. 98-33837, 98-33834, 99-56991 and 99-58816.

The polyester resin in the present invention is an aliphatic polyester resin which has superior physical properties sufficient to resolve the limitations used to be present in the conventional biodegradable types of resins by improved biodegradability ascribed to its peculiar molecular structure.

The specific properties of the biodegradable polyester resin in the present invention can be represented as shown in the following Table 1.

TABLE 1

| MP(° C.) | Injection (° C.) | Tensile Strength (kg/cm$^2$) | Elongation (%) | Decomposition (%) |
|---|---|---|---|---|
| 40–70 | 130–140 | 330 | 700 | 98 |
| 90 | 140–150 | 350 | 700 | 96 |
| 100 | 150–160 | 400 | 600 | 94 |
| 110–150 | 160–170 | 400 | 300 | 90 |

In the case of extrusion molding for the above polyester resins, according to the present invention, it is preferred to apply in producing flexible PVC materials such as a hose or an infusion bag, wherein the appropriate melting point of the resin ranges from 40 to 100° C., preferably from 70 to 100° C. If the melting point is below the above range the forming becomes hard to adjust properly due to low crystallinity while the product becomes too hard and thus the quality of the product may be deteriorated if it exceeds the above range.

Injection molding is generally used in producing relatively hard and durable parts of an infusion set made of either PP or ABS, and its appropriate melting temperature ranges from 100 to 120° C., more preferably from 105 to 120° C.; however, if the temperature is too low the quality of plastic infusion set becomes poor. The melting points of conventional polypropylene plastic infusion sets fall between 180 and 220° C. and thus the properties of those infusion sets are totally different from the one in the present invention. Injection or extrusion molding using the above biodegradable resins may be performed under general temperature conditions, however, the preferred temperature ranges from 120 to 190° C., and more preferably from 130 to 170° C. If the molding is performed at a temperature lower than 120° C. it is hard to produce a desirable infusion set product because the resin within the screw will not be completely melted while physical properties become poor due to heat decomposition if it is performed at a temperature higher than 190° C. The conventional types of resins have different molding temperature range, e.g., 230–275° C. for PP resin, 220–250° C. for ABS resin, and 150 to 190° C. for PVC. However, if the resins in the present invention are molded under temperatures used for conventional resins, the resins will not be appropriate for molding because they will be easily decomposed by heat and subsequently their physical properties will become extremely poor. Further, if the resins in the present invention are kept to stay within the screw of injection or extrusion for more than 10 min the molding cannot be well proceeded and the subsequent product would not be able to carry the proper properties of the infusion set even if they are molded.

For the production of highly durable infusion sets, the resin may be combined with strength fortifying additives selected from talc, calcium carbonate, magnesium stearate, calcium sulfate, starches, sugar powder, particular anhydrous silicate, calcium phosphate, and more preferably by adding 1–60 wt. % of talc or calcium carbonate based on the 1.00% by weight of resin, which then enables to improve the strength of the resins in the present invention comparable to the conventional resins such as polypropylene, polystyrene or ABS resin. Calcium carbonate is inferior to talc in fortifying strength, however, it can be served as a fertilizer and prevent the soils from being acidified when it becomes degraded in nature and left on the surface of soils after burial. In addition, the combustion rate of calcium carbonate added resin was better than those of resin alone or talc-added resin in the present invention.

The infusion sets in the present invention include not only the set product consisting of an infusion bag, a hose and its appended parts but also include storage sets and other similar products.

Figure 2:
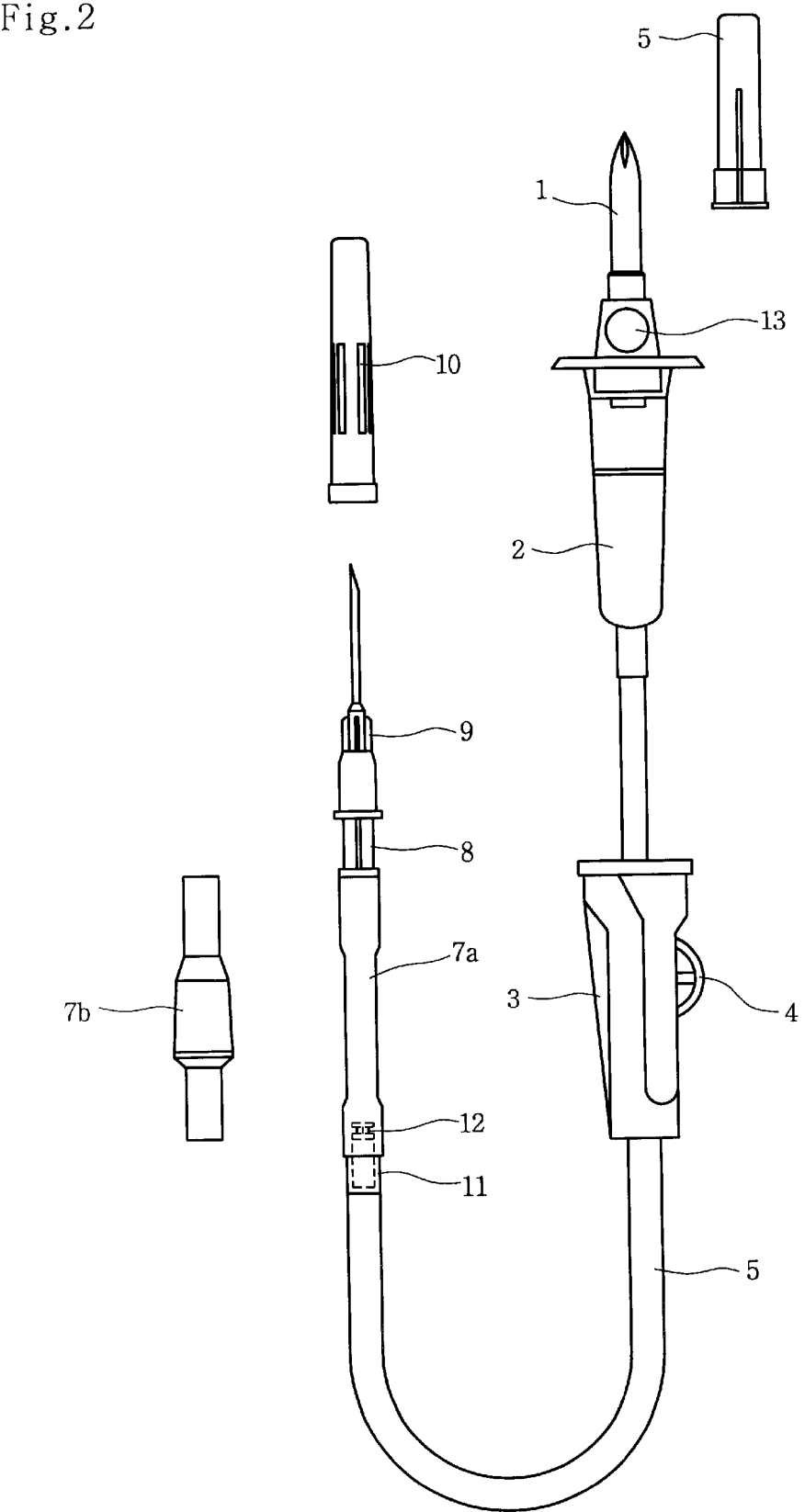
FIG. 2 shows the schematic view of a hose and appended parts of another example of biodegradable infusion sets manufactured according to the method of the present invention.

For example, FIG. 1 shows an example of an infusion bag and a hose of a biodegradable infusion set manufactured using polyester resin composition of the present invention. FIG. 2 schematically shows another example of a hose and appended parts of the infusion sets manufactured according to the method of the present invention and they consist of parts such as spike 1, chamber 2, clamp 3, roller 4, spike cover 5, tube 6, rubber tube (straight) 7a, rubber tube (convex) 7b, adapter 8, bulk 9, cap 10, joint 11, final filter 12 and air filter 13. Here, the parts 3, 4, 5, 8 and 10 are manufactured by an injection molding while the parts 2, 6 and 11 are manufactured by an extrusion molding.

Figure 3:
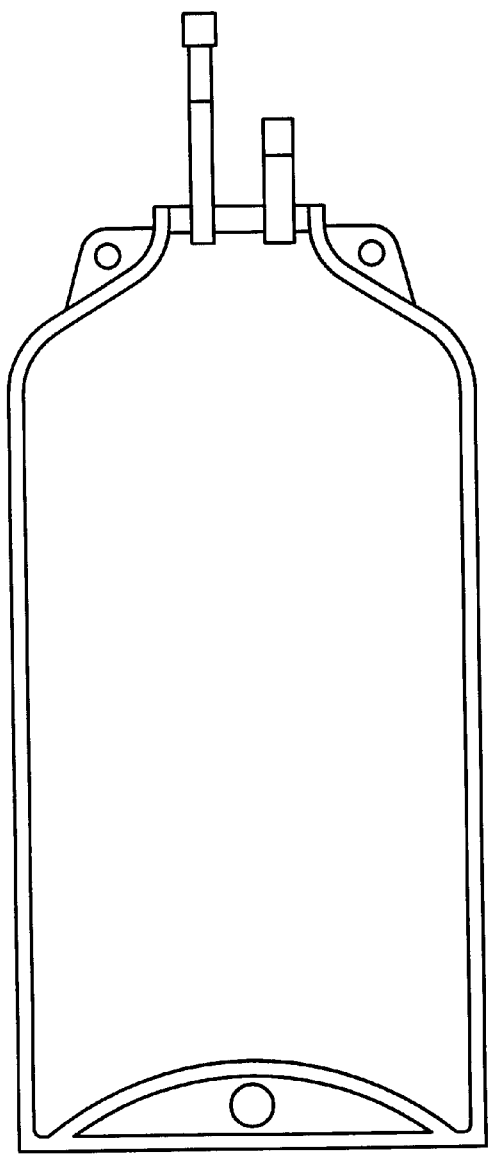
FIG. 3 shows an example of an infusion bag of the biodegradable infusion set manufactured according to the method of the present invention.

FIG. 3 shows one example of infusion bags of the biodegradable infusion sets manufactured using polyester resin composition according to the method of the present invention.

The following examples are intended to be illustrative of the present invention and should not be construed as limiting the scope of this invention defined by the appended claims.

PREPARATION EXAMPLE 1

To a 500 mL Erlenmeyer's flask filled with nitrogen gas, 29.9 g of adipic acid, 95.6 g of succinic acid and 3 g of 2-amino-5-hydroxybenzoic acid were added and esterified while slowly increasing the temperature until it reaches 200° C. and water was effused out. When the temperature reached 200° C., the theoretical mass of water was effused out completely. Then, 130 g of 1,4-butanediol and 0.1 g of tetrabutyltitanate, a catalyst, were added to the reaction mixture under nitrogen gas and the mixture was allowed to react at 200° C. for 2 hrs and then theoretical mass of water was effused. 0.1 g of antimony acetate, 0.2 g of dibutyltin oxide, 0.07 g of tetrabutyltitanate as catalysts, and 0.2 g of trimethyl phosphate as a stabilizer were added to the reaction mixture. The temperature was raised until it reached 245° C. and a polycondensation reaction was performed under 0.3 torr at 245° C. for 210 min. The sample of biodegradable resin taken at this point had a melting viscosity of 9 (190° C., 2160 g), number average molecular weight of 41,000, weight average molecular weight of 270,000 and melting point of 90° C. as measured by DSC method.

PREPARATION EXAMPLE 2

To a 500 mL Erlenmeyer's flask filled with nitrogen gas 118 g of succinic acid, 121.7 g of 1,4-butanediol and 0.1 g of tetrabutyltitanate as a catalyst, were added while slowly increasing the temperature until it reached 200° C. When the temperature reached 200° C., the reaction mixture was allowed to react for 2 hrs and then theoretical mass of water was effused. Then 0.1 g of antimony acetate, 0.2 g of dibutyltin oxide, 0.07 g of tetrabutyltitanate as catalysts, and 0.2 g of trimethyl phosphate as a stabilizer were added. The temperature was raised until it reached 245° C. and a polycondensation reaction was performed under 0.3 torr at 245° C. for 155 min. The sample of biodegradable resin taken at this point had a melting viscosity of 15 (190° C., 2160 g), number average molecular weight of 31,000, weight average molecular weight of 190,000 and melting point of 117° C. as measured by DSC method.

PREPARATION EXAMPLE 3

To a 500 mL Erlenmeyer's flask filled with nitrogen gas was added 5.9 g of succinic acid, 6.3 g of 1,4-butanediol and 0.1 g of tetrabutyltitanate, a catalyst, and water was effused by means of esterification while slowly increasing the temperature until it reached 205° C. When the temperature reached 205° C., theoretical amount of water was effused completely out to produce 8.6 g of aliphatic low molecular weight polymer with its molecular weight around 3,000. Then, 76.1 g of terephthalic acid, 135.2 g of 1,4-butanediol, and 0.2 g of tetrabutyltitanate, a catalyst, were added to the reaction mixture and methanol was effused completely at 205° C. and 29.5 g of succinic acid and 43.8 g of adipic acid were added for esterification. Here, the temperature was set at 180° C. and after water was effused completely and 0.1 g of antimony trioxide, 0.3 g of dibutyltin oxide, 0.07 g of tetrabutyltitanate as catalysts, and 0.1 g of trimethyl phosphate as a stabilizer were added. The temperature was raised until it reached 245° C. and a polycondensation reaction was performed under 0.3 torr at 245° C. for 180 min. The sample of biodegradable resin taken at this point had a melt index of 2 (190° C., 2160 g), number average molecular weight of 61,000, weight average molecular weight of 290,000 and melting point of 117° C. as measured by DSC method.

PREPARATION EXAMPLE 4

To a 500 mL Erlenmeyer's flask filled with nitrogen gas, 8.5 g of dimethyl terephthalate and 25 g of 1,4-butanediol were added while slowly increasing the temperature until it reached 200° C. When the temperature reached 200° C., methanol was effused completely out by means of ester-substitution reaction. 5.9 g of succinic acid, 7.3 g of adipic acid were added and adjusted the temperature to 180° C. to produce 28 g of aromatic/aliphatic low molecular weight polymer with its molecular weight around 10,000 by effusing the water completely by means of esterification. Then, 107 g of succinic acid, 1.35 g of 1,4-butanediol, 14.6 g of adipic acid and 0.4 g of tetrabutyltitanate, a catalyst, were added to the reaction mixture under nitrogen gas and temperature was raised until it reached 200° C. When the temperature reached 200° C., the reaction mixture was allowed to react for 2 hrs and then theoretical mass of water was effused. To the above was added 0.1 g of antimony acetate, 0.2 g of dibutyltin oxide, 0.07 g of tetrabutyltitanate as catalysts, and 0.2 g of trimethyl phosphate as a stabilizer. The temperature was raised until it reached 245° C. and a polycondensation reaction was performed under 0.3 torr at 245° C. for 200 min. The sample of biodegradable resin taken at this point had a melt index of 7 (190° C., 2160 g), number average molecular weight of 39,000, weight average molecular weight of 290,000 and melting point of 98° C. as measured by DSC method.

EXAMPLE 1

Infusion sets(the hose and appended parts only) were manufactured by using polyester resins having 90° C. and 98° C. of melting points produced in the above Preparation Examples 1 and 4 under 130–150° C. by means of extrusion molding. The test results showed that infusion sets had 450 kg/cm$^2$ and 460 kg/cm$^2$ for tensile strength, 600% and 630% for elongation, and 98% and 97% for biodegradability rate after 45 days, respectively. The biodegradability was measured by Organic Waste Systems[O.W.S.n.v.](Dok Noord 4, B-9000 Gent, Belgium), and tensile strength and elongation were measured by UTM.

EXAMPLE 2

Infusion sets(durable appended parts only) were manufactured by using polyester resin having 117° C. of melting point produced in the above Preparation Examples 2 and 3 under 150–170° C. by means of injection molding. The test results of infusion sets showed 400 kg/cm 2 and 420 kg/cm 2 of tensile strength, 300% and 320% of elongation, and 90% and 94% of biodegradability rate after 45 days. The biodegradability was measured by Organic Waste Systems [O.W.S.n.v.](Dok Noord 4, B-9000 Gent, Belgium), and tensile strength and elongation were measured by UTM.

What is claimed is:

1. A plastic infusion set manufactured by means of injection and extrusion molding using biodegradable polyester resin composition having number average molecular weight of 9,000–90,000, weight average molecular weight of 30,000–600,000, melting point of 40–150° C., a melt index (190° C., 2160 g) of 0.1–50 g/min, and wherein said polyester resin consists essentially of:

an aromatic dicarboxylic acid;

an aliphatic dicarboxylic acid selected from the group consisting of succinic acid, adipic acid, and combinations thereof; and an aliphatic glycol.

2. A biodegradable plastic infusion set in accordance with claim 1, wherein said polyester resin composition includes talc or calcium carbonate.

3. A biodegradable plastic infusion set in accordance with claim 2, wherein the flexible infusion bag and hose of said infusion set comprises a polyester resin having a melting point of 40–100° C., and the appended parts of said infusion set comprises a polyester resin having a melting point of 105–120° C.

4. A biodegradable plastic infusion set in accordance with claims 1, wherein said injection and extrusion moldings are performed at 130–170° C.

5. A biodegradable plastic infusion set in accordance with claim 1, wherein the types of said infusion set includes a set comprising an infusion bag, a hose, appended parts and a storage set.

6. A biodegradable plastic infusion set in accordance with claim 1 wherein:

said aromatic dicarboxylic acid is selected from the group consisting of dimethyl phthalate, terephthalic acid, and combinations thereof; and said aliphatic glycol is selected from the group consisting of 1,4-butanediol and ethylene glycol, and combinations thereof.

7. A biodegradable plastic infusion set in accordance with claim 1 wherein one or more of said aromatic dicarboxylic acid and aliphatic dicarboxylic acid is an acid anhydride thereof.

* * * * *